US008404479B2

(12) United States Patent
Shimizu et al.

(10) Patent No.: US 8,404,479 B2
(45) **Date of Patent: *Mar. 26, 2013**

(54) SIMPLE MEMBRANE ASSAY METHOD AND KIT

(75) Inventors: Hideharu Shimizu, Gosen (JP); Takeshi Watanabe, Gosen (JP); Kazuyuki Takizawa, Gosen (JP); Junji Matsuda, Gosen (JP); Toshinori Sato, Gosen (JP)

(73) Assignee: Denka Seiken Co., Ltd, Tokyo (JP)

( * ) Notice: Subject to any disclaimer, the term of this patent is extended or adjusted under 35 U.S.C. 154(b) by 210 days.

This patent is subject to a terminal disclaimer.

(21) Appl. No.: 12/458,662

(22) Filed: Jul. 20, 2009

(65) Prior Publication Data

US 2009/0286226 A1 Nov. 19, 2009

Related U.S. Application Data

(60) Division of application No. 11/471,622, filed on Jun. 21, 2006, now Pat. No. 7,579,195, which is a continuation of application No. PCT/JP03/16615, filed on Dec. 24, 2003.

(51) Int. Cl.
*C12M 1/34* (2006.01)

(52) U.S. Cl. ..................... 435/287.2; 422/405; 422/420; 422/422; 422/427; 422/430; 435/287.7; 435/287.9; 435/288.1; 435/810

(58) Field of Classification Search .................. 422/405, 422/422, 420, 427, 430, 524; 435/7.1
See application file for complete search history.

(56) References Cited

U.S. PATENT DOCUMENTS 4,270,923 A 6/1981 Kondo et al.
4,693,834 A 9/1987 Hossom
4,727,019 A 2/1988 Valkirs et al.
4,943,522 A 7/1990 Eisinger et al.
4,948,561 A 8/1990 Hinnkley et al.
5,008,080 A 4/1991 Brown, III et al.
5,030,555 A 7/1991 Clemmons
5,149,622 A 9/1992 Brown et al.
5,202,267 A 4/1993 Ditlow et al.

(Continued)

FOREIGN PATENT DOCUMENTS

JP 61-73054 4/1986
JP 3-503807 8/1991

(Continued)

OTHER PUBLICATIONS

Extended European Search Report dated Nov. 30, 2010 issued in corresponding European Application No. 10011767.0-1223.

(Continued)

*Primary Examiner* — Chris L Chin
(74) *Attorney, Agent, or Firm* — Nixon & Vanderhye P.C.

(57) ABSTRACT

A simple membrane assay method for detecting or quantitating an analyte in a specimen sample using an assay device equipped with a membrane bound with a capture-substance to capture the analyte, including the steps of filtering a specimen sample using a filter, dropping the filtrate onto said membrane and detecting the presence of the analyte in said specimen sample, as well as a simple membrane assay kit for detecting the presence of an analyte in a specimen sample, including (1) a filter tube, and (2) an assay device equipped with a membrane bound with a capture-substance to capture the analyte. The method or the kit can decrease the occurrence of false positivity and can provide a highly accurate detection of the analyte such as pathogen and antibody in a specimen collected in a medical scene or by an individual.

11 Claims, 3 Drawing Sheets

U.S. PATENT DOCUMENTS

| | | | | |
|---|---|---|---|---|
| 5,231,035 | A | 7/1993 | Akers, Jr. | |
| 5,252,458 | A * | 10/1993 | Liav et al. | 435/5 |
| 5,252,496 | A | 10/1993 | Kang et al. | |
| 5,339,829 | A * | 8/1994 | Thieme et al. | 600/573 |
| 5,354,692 | A | 10/1994 | Yang et al. | |
| 5,418,142 | A * | 5/1995 | Kiser et al. | 435/14 |
| 5,559,041 | A | 9/1996 | Kang et al. | |
| 5,573,009 | A * | 11/1996 | Thieme et al. | 600/573 |
| 5,728,587 | A | 3/1998 | Kang et al. | |
| 5,786,227 | A * | 7/1998 | Charlton | 436/177 |
| 5,837,546 | A | 11/1998 | Allen et al. | |
| 6,027,943 | A | 2/2000 | Kang et al. | |
| 6,090,572 | A | 7/2000 | Crosby | |
| 6,207,445 | B1 | 3/2001 | Crosby | |
| 6,221,655 | B1 | 4/2001 | Fung et al. | |
| 6,506,612 | B2 | 1/2003 | Kang et al. | |
| 6,541,277 | B1 | 4/2003 | Kang et al. | |
| 7,544,324 | B2 * | 6/2009 | Tung et al. | 422/504 |
| 2002/0160525 | A1 | 10/2002 | Kang et al. | |

FOREIGN PATENT DOCUMENTS

| | | |
|---|---|---|
| JP | 4289456 | 10/1992 |
| JP | 6-050973 | 2/1994 |
| JP | 06-324037 | 11/1994 |
| JP | 06-331625 | 12/1994 |
| JP | 9-501494 | 2/1997 |
| JP | 9061429 | 3/1997 |
| JP | 10185920 | 7/1998 |
| JP | 10211277 | 8/1998 |
| JP | 11-316222 | 11/1999 |
| JP | 2000-502452 | 2/2000 |
| JP | 2000-088851 | 3/2000 |
| JP | 2000-088854 | 3/2000 |
| JP | 2001-124775 | 5/2001 |
| JP | 3079968 | 6/2001 |
| JP | 2001-296297 | 10/2001 |
| JP | 2002-116206 | 4/2002 |
| JP | 3088698 | 7/2002 |
| WO | WO 87/01393 | 3/1987 |
| WO | WO90/09588 | 8/1990 |
| WO | WO 95/04280 | 2/1995 |
| WO | WO 97/23781 | 7/1997 |
| WO | WO 00/00265 | 1/2000 |

OTHER PUBLICATIONS

Tucker et al, "A flu optical immunoassay (ThermoBioStar's FLU OIA): a diagnostic tool for improved influenza management", The Royal Society. Phil. Trans. R. Soc. Lond. B (2001) vol. 356, pp. 1915-1924.

International Search Report mailed May 18, 2004 in PCT/JP2003/016615.

Supplementary European Search Report dated Jul. 3, 2007, issued in counterpart European Application No. 0378 6278.6.

European Official Action dated Oct. 8, 2008, issued in counterpart European Application No. 03 786 278.6-1223.

Japanese Office Action (Questioning Interrogation) issued for corresponding Japanese Patent Application No. 2006-99040 dated Sep. 2, 2010.

Japanese Office Action issued for corresponding Japanese Patent Application No. 2006-099040 dated May 18, 2009.

Japanese Office Action issued for corresponding Japanese Patent Application No. 2008-214432 dated Sep. 1, 2011.

Japanese Final Office Action issue for corresponding Japanese Patent Application No. 2006-099040 dated Aug. 11, 2011 with Partial Translation.

Pamphlet of "Influ A & B-quick-Seiken-, a kit for detecting antigen of influenza virus type A or B by EIA method", Sep. 2001, Denka Seiken Co., Ltd.

Package insert of "Influ A & B-quick-Seiken-, a kit for detecting antigen of influenza virus type A or B by EIA method", revised on Oct. 2001, Denka Seiken Co., Ltd.

* cited by examiner

SIMPLE MEMBRANE ASSAY METHOD AND KIT

CROSS-REFERENCE TO RELATED APPLICATION

This application is a Divisional of application Ser. No. 11/471,622, filed Jun. 21, 2006, which was a continuation of PCT/JP2003/016615, filed Dec. 24, 2003, the entire content of each of which is hereby incorporated by reference.

TECHNICAL FIELD

The present invention relates to an assay method for detecting or quantitating a certain substance in a specimen using an assay device equipped with a membrane, specifically to a simple membrane assay method which can be used clinically and to a kit used for this method.

BACKGROUND ART

Recently, there have been developed simple assay reagents or kits wherein various measuring items including the infection with pathogens such as viruses and bacteria, the presence of pregnancy and blood-sugar level can be detected or quantitated in a short time of from a few minutes to several tens minutes using antigen-antibody reactions, enzyme reactions and the like. Proteins composing pathogens, human chorionic gonadotropin (hCG), blood-sugar and the like are the subjects of the detection or quantitation. Most of the simple assay reagents have the characteristics that they do not require any special equipment, their operations are also easy and they are low in price. For example, a simple assay reagent for pregnancy diagnosis is sold in general drugstores under OTC. The simple assay reagents measuring the infection with pathogens are widely used also in general hospitals and clinics in addition to large hospitals and medical assay centers unlike other assay reagents. These places are often medical institutions where patients visit first. If the presence of infections in specimens collected from patients could be clarified there and then, therapeutic treatment can be applied in early stages of symptoms. The importance of such simple assay reagents or kits in medical field, therefore, is increasing more and more.

Presently, membrane assay methods, specifically assay methods using membrane such as film or filter of nitrocellulose and the like as simple test methods have been generally known, being roughly classified into flow-through type and lateral-flow type membrane assay methods. The former is a method wherein a solution containing a substance or an analyte to be examined is passed vertically through a membrane coated with a substance for detecting said analyte and the latter is a method developed in lateral direction. In both methods, they have a common point that the detection or quantitation of an analyte in a sample is performed by forming a complex of a membrane-immobilized substance which specifically binds to the analyte, the analyte and a labeled substance which specifically binds to the analyte on a film, and then by detecting or quantitating said labeled substance.

However, when a specimen practically collected from a patient is analyzed by such simple membrane assay method using membranes or filters, so-called "false positive" or "false positivity", which is a positive judgment made in spite of the absence of an analyte in the specimen, may occur. The occurrence of false positive reaction during measuring the infection with pathogens leads to mistaken information on the patient. Therefore, not only the specification of the cause may be delayed, but also an inappropriate treatment may be taken to lead to serious consequence such as aggravation of the condition of a disease to more severe. Accordingly, suppression of false positive reaction is an extremely important issue in view of the major purpose of use of a simple test method.

Until now, for a so-called immunoassay, a method diluting the sample with a buffer containing a surfactant (for example, JP-A-9-501494), a method absorbing by absorbent filter containing a surfactant (for example, JP-A-2000-502452) and the like have been reported, but they have not been sufficient (the term "JP-A" as used herein means an "unexamined published Japanese patent application").

SUMMARY OF THE INVENTION

An object of the present invention is to provide a simple assay method of testing a specimen using a membrane assay method, wherein the method can inhibit the occurrence of false positivity and can detect or quantitate an analyte with high accuracy, and a kit used in such a method.

In detecting and quantitating an analyte using a membrane assay method, it has been found that the occurrence of false positivity can be greatly inhibited by filtering a possible specimen sample containing the analyte through a filter.

That is to say, an object of the present invention can be achieved by a simple membrane assay method for detecting or quantitating an analyte in a specimen sample using an assay device equipped with a membrane bound with a capture-substance to capture the analyte, comprising the steps of filtering the specimen sample using a filter, dropping the filtrate onto the membrane and detecting the presence of the analyte in said specimen sample.

In addition, an object of the present invention can be achieved by a simple membrane assay kit for detecting the presence of an analyte in a specimen sample, comprising:

(1) a filter tube for specimen sample equipped with a filter; and (2) an assay device equipped with a membrane bound with a capture-substance to capture the analyte.

The another embodiment relates to the above-mentioned method or kit, characterized in that the material of the filter is selected from the group consisting of nonwoven fabric, paper, glass fiber, silica fiber, nitrocellulose, cellulose ester, a mixture of nitrocellulose and cellulose ester, polyether sulfone, polysulfone, polyethylene tetrafluoride, polyvinylidene fluoride, polycarbonate, polypropylene, polyamide, 6,6-nylon, polyester, cotton, stainless steel fiber and a combination thereof.

The preferred embodiment is the above-mentioned method or kit, wherein the pore size of the filter or the particle retention size of said filter is from 0.2 to 8.0 μm. The pore size or the particle retention size of said filter is more preferably from 0.2 to 4.0 μm, even more preferably from 0.2 to 2.0 μm, and most preferably from 0.2 to 0.6 μm in view of the effect of the present invention.

Moreover, the another preferred embodiment according to the present invention is the above-mentioned method or kit, wherein said filter is a glass fiber filter, a nitrocellulose filter, or a combination of glass fiber filter and nitrocellulose filter.

Furthermore, the another preferred embodiment according to the present invention is the above-mentioned method or kit, wherein the material of said membrane is selected from the group consisting of nonwoven fabric, paper, nitrocellulose, glass fiber, silica fiber, cellulose ester, polyether sulfone, polysulfone, polyethylene tetrafluoride, polyvinylidene fluoride, polycarbonate, polypropylene, polyamide, 6,6-nylon and a mixture of cellulose ester and nitrocellulose, and the pore size or the particle retention size of said membrane is not less than the pore size or the particle retention size of said filter and is from 0.3 to 15 μm.

The another more preferred embodiment according to the present invention is the above-mentioned method or kit, wherein the above-mentioned material of the membrane is nitrocellulose and its pore size is from 0.4 to 12 μm.

Moreover, the another preferred embodiment according to the present invention is the above-mentioned method or kit, wherein said analyte in the specimen sample is an influenza virus.

In addition, particularly preferred embodiment according to the present invention is the above-mentioned method or kit concerning a flow-through type or lateral-flow type of simple membrane assay method or kit.

In the case of a flow-through type of membrane assay method or assay kit, the pore size or the particle retention size of the filter is preferably from 0.2 to 4.0 μm, more preferably from 0.2 to 2.0 μm, and most preferably from 0.2 to 0.6 μm. In the case of a lateral-flow type of membrane assay method or assay kit, the pore size or the particle retention size of the filter is preferably from 0.2 to 8.0 μm, more preferably from 0.2 to 4.0 μm, even more preferably from 0.2 to 2.0 μm, and most preferably from 0.2 to 0.6 μm.

According to the method of the present invention, in a simple membrane assay method using an assay device equipped with a membrane bound with a capture-substance to capture an analyte, the occurrence of false positivity could be greatly decreased. The rationale for the effect would be considered as follows but not limited thereto. In a simple membrane assay method using an assay device equipped with a membrane bound with a capture-substance to capture an analyte, the specimen is collected by wiping the site where the analyte is predicted to exist, for example, the pharynx, nasal cavity or the like of a patient to suspend into a buffer, or a portion of secretion or excretion containing the analyte such as nasal discharge or urine is collected and diluted with a buffer to prepare a sample for the membrane assay. In this case, besides the materials to be measured, cells peeled off from the sampling site, or components of the secretion or excretion may be contaminated into said sample. Because various biological components including viscous substance such as proteoglycan and glycolipid are contained in such the contaminant, if said sample is added onto a membrane directly, some components may be adhered onto or into the membrane. Particularly membranes whose pore size or the particle retention size is from 0.1 to 10 μm are often used. When a component with a size equivalent to such the pore size or the particle retention size is added, it is considered that the component may block the pores in the membrane and then inhibit the movement of the ingredients in the solution. It is considered that non-specific reactions may occur due to such a phenomenon and then so-called false positivity may be occurred, wherein it is judged to be positive in spite of the absence of the analyte in the sample. Such a false positivity could be inhibited effectively according to the method of the present invention, and then a highly reliable simple test method could be established.

Figure 1:
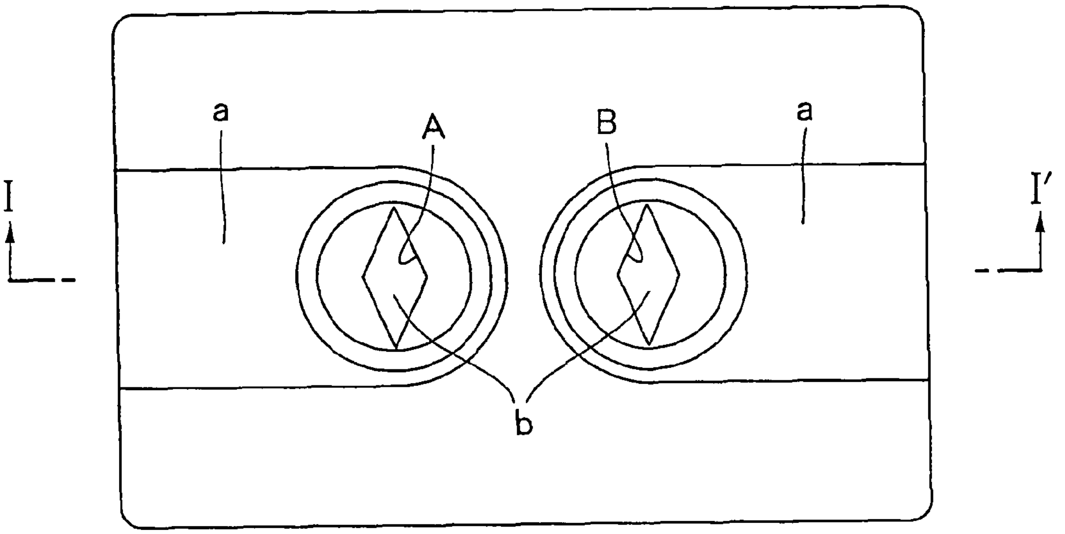
FIG. 1 is a plane view of a flow-through type membrane assay device that is one embodiment according to the present invention.

In each Figure, each sign refers to as follows:

A: hole, B: hole, a: adapter, b: membrane, c: liquid absorbing pad, d: filter tube tip part, e: filter tube body part, f filter, g: sample receiving pad, h: substrate receiving pad, i: absorption pad, j: nitrocellulose membrane, k: line coated with anti-influenza B type virus NP monoclonal antibody, l: line coated with anti-influenza A type virus NP monoclonal antibody, m: backing sheet.

BEST MODE FOR CARRYING OUT THE INVENTION

The present invention is described in detail below.

[Simple Membrane Assay Method]

The method according to the present invention is a simple membrane assay method for detecting or quantitating an analyte in a specimen sample using an assay device equipped with a membrane bound with a capture-substance to capture the analyte, characterized in that the specimen sample is filtered using a filter followed by dropping the filtrate onto said membrane and then the presence of the analyte in said specimen sample is detected or quantitated.

As used herein, "a simple membrane assay method" refers to a method wherein the presence of an analyte in a specimen sample is simply tested in a short time using an assay device comprising a membrane in which a capture-substance that specifically binds to the analyte is in the solid phase. Typically, it is a method wherein an analyte is reacted with said capture-substance and a labeled detection-reagent to form a sandwich complex on the membrane, and then the presence of this complex is detected by detecting said label. The examples of reaction of the analyte with said capture-substance or labeled detection-reagent include antigen-antibody reaction, another reaction between acceptor and receptor, specific binding reaction between biotin and avidin, reaction between DNAs having complementary sequence each other and the like. Moreover, the simple assay method according to the present invention may be used for any kind of the analyte or may use any kind of the membrane or the labeled substance without limitation as far as they are used in such a method.

The membrane assay method according to the present invention is preferably selected from two kinds of membrane assay method, one of which is a flow-through type membrane assay method and the other is a lateral-flow type membrane assay method, because these methods are simple and rapid. The flow-through type membrane assay method is a method wherein a solution containing an analyte is passed vertically through a membrane having a capture-substance immobilized thereon, which binds specifically to the analyte or a substance for detecting the analyte. In this method, the detection or quantitation of the analyte is conduced by forming a complex of the capture-substance which binds specifically to the analyte, the analyte and the labeled substance which binds specifically to the analyte on the membrane followed by detecting or quantitating the label. The lateral-flow type membrane assay method is different from the flow-through type membrane assay method in that it uses a similar membrane to develop the solution containing the analyte in lateral direction against the membrane, but its detection principle is similar to that of the flow-through type membrane assay method.

One example of concrete procedures for the method according to the present invention is shown below to illustrate the present invention.

(1) A specimen sample collected from the pharynx or nasal cavity, etc. of a patient infected with virus, bacteria or the like is suspended in a specimen suspension as described below.

(2) The suspension is placed into a filter tube for specimen sample equipped with a filter and is filtered through the filter.

(3) The filtrate is dropped onto a membrane bound with a capture-substance which binds specifically to the analyte in an assay device equipped with the membrane to capture the analyte, and then the analyte is allowed to be captured on the membrane.

(4) A labeled detection-reagent which binds specifically to the analyte is dropped onto said membrane to form a complex of the capture-substance/analyte/labeled detection-reagent on it.

(5) The presence of the analyte in the specimen sample is determined by detecting the presence of the complex through the labeled detection-reagent in said complex.

[Filter]

In the method according to the present invention, a specimen sample collected from a patient is dissolved or suspended in a solution for dissolving or suspending a specimen followed by filtration of the suspension or solution using a filter. The pore size (diameter) of the filter or the particle retention size of the filter is preferably from 0.2 to 8.0 μm, more preferably from 0.2 to 4.0 μm, even more preferably from 0.2 to 2.0 μm, and most preferably from 0.2 to 0.6 μm. Moreover, in the flow-through type membrane assay method and flow-through type membrane assay kit, the pore size (diameter) or the particle retention size of the filter is particularly preferably from 0.2 to 4.0 μm, more preferably from 0.2 to 2.0 μm, and most preferably from 0.2 to 0.6 μm. Further, in the lateral-flow type membrane assay method and lateral-flow type membrane assay kit, the pore size (diameter) or the particle retention size of the filter is preferably from 0.2 to 8.0 μm, more preferably from 0.2 to 4.0 μm, even more preferably from 0.2 to 2.0 μm, and most preferably from 0.2 to 0.6 μm.

The pore size or the particle retention size of the filter is important for the effect of the present invention. If the pore size or the particle retention size of the filter is too large, in some case, a non-specific binding may occur on the membrane to result in a false positivity. Conversely, if it is too small, filter itself may be plugged due to any viscous substances or agglomerates present in the sample resulting in impracticable filtration, or the area of filter must be relatively widened. This is not suitable in view of the purpose of the filter to be used for a simple test method.

Not only a kind of the filter, but also a combination of filters whose materials and/or the pore size or the particle retention size are different from each other may be used. In the case that a combination filter (that is, plural filters in a combined form) is used, the smallest pore size or the smallest particle retention size among those of the plural filters is considered to be the combination filter's pore size or particle retention size. Then, if at least one filter in a combination filter has the pore size or the particle retention size within from 0.2 to 8.0 μm, more preferably from 0.2 to 4.0 μm, even more preferably from 0.2 to 2.0 μm, and most preferably from 0.2 to 0.6 μm, there is no problem even if the pore size or the particle retention size of the other filters in the combination filter are beyond said range.

In addition, a combination of two or more of the same filters provides an advantage of being able to obtain a certain effect even if filters whose pore size or the particle retention size vary widely are used. Further, when any inadequate filters in strength are used, two or more filters can be accumulated to increase the strength of the resulting filter. Accumulating multiple filters, however, has also a disadvantage that the resulting filter is easy to be plugged, the pressure to filter increases and then the simplicity is lost, depending on the kind of filter.

The material of the filter includes, but not limited to, non-woven fabric, paper, glass fiber, silica fiber, nitrocellulose, cellulose ester, a mixture of nitrocellulose and cellulose ester, polyether sulfone, polysulfone, polyethylene tetrafluoride, polyvinylidene fluoride, polycarbonate, polypropylene, polyamide, 6,6-nylon, polyester, cotton, stainless steel fiber and the like. Glass fiber and nitrocellulose are preferable.

Filters are generally divided into depth-filter and screen-filter depending on collecting mechanism. The depth-filter is what collects solid matter inside it, while the screen-filter is what collects solid matter on the surface of the filter. The filters with both the mechanisms can be preferably used.

[Filter Tube]

Figure 3:
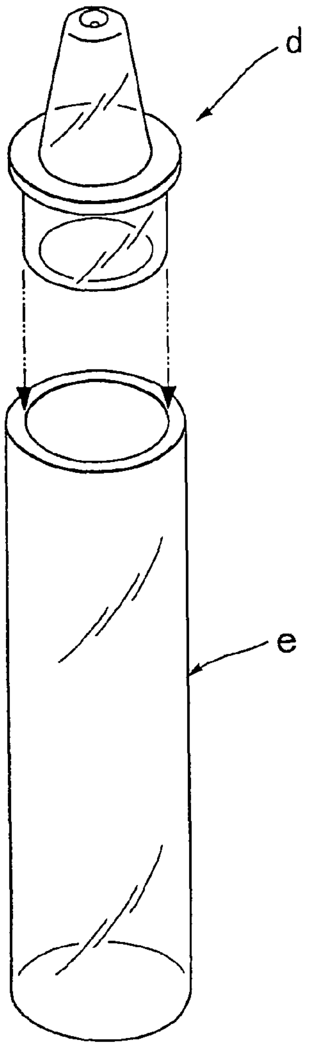
FIG. 3 shows one embodiment of a filter tube for specimen sample used in the present invention.
Figure 4:
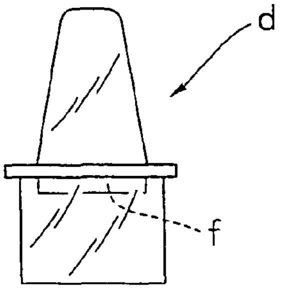
FIG. 4 shows a perspective view of the tip part of the filter tube for specimen sample of FIG. 3.

The above filter is preferably attached at the tip of a filter tube for specimen sample to use in the simple membrane assay method or kit according to the present invention. That is to say, a method, wherein a specimen sample suspended in a suspension is placed into the filter tube, filtered through the filter attached at the tip of the filter tube, and then the filtrate is dropped onto the membrane in the membrane assay device, is simple and preferable. The schematic diagrams of one embodiment of this filter tube are shown in FIG. 3 and FIG. 4. The filter tube is a shape consisting of a tip part and a body part, for example, as described in FIG. 3. A filter is equipped inside the tip part, as shown in FIG. 4. A suspension of specimen sample is placed in the body part and the tip part equipped with the filter is attached to the body part. The specimen sample is filtered through the filter, and then the filtrate is dropped onto the membrane assay device. The body part is preferably made of flexible material such as polyethylene and polyethylene terephthalate (PET) since the specimen sample can be easily filtered by applying pressure with hand or the like in the tube attached with the filter.

[Assay Device]

An assay device equipped with a membrane (also referred to as a membrane assay device), as used herein, is a device comprising a membrane having a capture-substance immobilized thereon or in solid phase, which binds specifically to an analyte. Such an assay device is preferably a device using a flow-through type membrane assay method or a lateral-flow type membrane assay method. The example of the assay device using a flow-through type membrane assay method is, for example, a device as shown in FIGS. 1 and 2.

Figure 2:
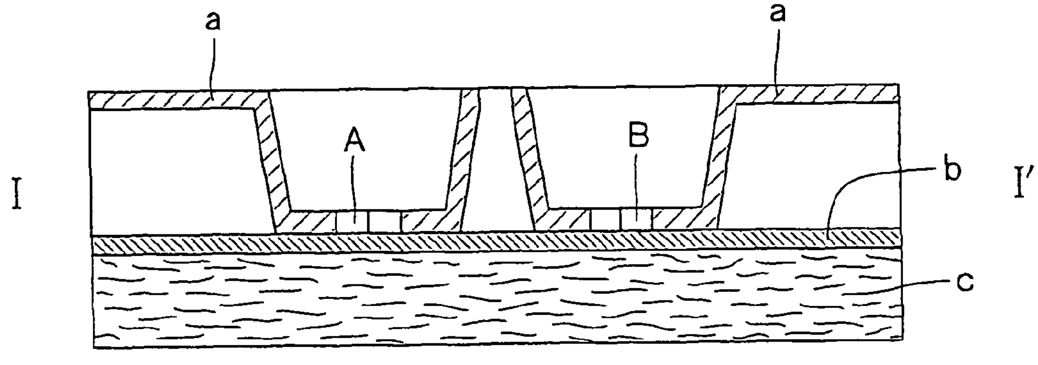
FIG. 2 is an end view through a cutting-plane line I-I' of FIG. 1.

FIG. 1 is a plane view of the flow-through type device, and FIG. 2 is an end view through a cutting-plane line I-I' of FIG. 1. “a” is an adapter which has an opening to drop a prepared specimen sample and which is equipped with holes (“A” hole and “B” hole) to pass the sample to the bottom. “b” is a membrane bound with a capture-substance which binds specifically to an analyte. “c” is a liquid absorbing pad.

Figure 5:
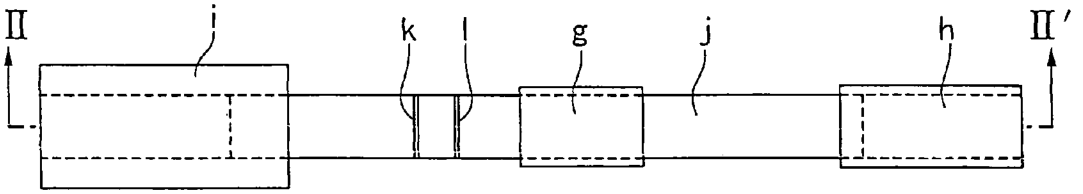
FIG. 5 is a plane view of a lateral-flow type membrane assay device that is one embodiment according to the present invention.
Figure 6:
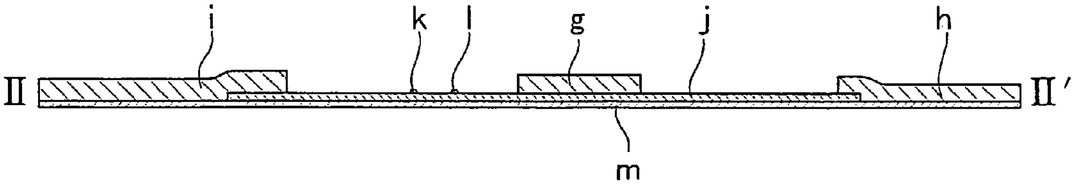
FIG. 6 is an end view through a cutting-plane line II-II' of FIG. 5.

The example of the assay device using a lateral-flow type membrane assay method is, for example, a device as shown in FIGS. 5 and 6.

FIG. 5 is a plane view of the lateral-flow type device, and FIG. 6 is an end view through a cutting-plane line II-II' of FIG. 5. “g” is a pad which is installed to receive a prepared specimen sample and which allows a labeled detection-reagent to be contained in a dry state. "h" is a pad which is installed to receive a substrate for the enzyme and "i" is a pad to absorb a dropped solution. "j" is a membrane bound with a capture-substance which binds specifically to an analyte. "k" and "l" show the position where capture-substances which bind specifically to the analyte are bound on the "j" in the form of a line. "m" is a plastic backing sheet to fix the members of the device in order to increase the strength of the device.

[Membrane]

The material of the membrane in the membrane assay device includes the group consisting of nonwoven fabric, paper, nitrocellulose, glass fiber, silica fiber, cellulose ester, polyether sulfone, polysulfone, polyethylene tetrafluoride, polyvinylidene fluoride, polycarbonate, polypropylene, polyamide, 6,6-nylon as well as a mixture of nitrocellulose and cellulose ester. Microporous substance produced from nitrocellulose is particularly preferable. In addition, said mixture of cellulose ester and nitrocellulose can be preferably used. The pore size or the particle retention size of said membrane is not less than the pore size or the particle retention size of above-mentioned filter and it is preferably from 0.3 to 15 μm, particularly preferably from 0.4 to 12 μm. Moreover, the thickness of the membrane is not particularly limited, but it is generally within the order of from 100 to 200 μm.

[Analyte]

An analyte as used herein includes, but not limited to, virus antigen such as influenza virus, adenovirus, RS virus, HAV, HBc, HCV, HIV, EBV, Norwalk-like virus, etc., bacteria antigen such as *Chlamydia trachomatis, hemolytic streptococcus, Bordetella pertussis, Helicobacter pylori, Leptospira, Treponema pallidum, Toxoplasma gondii, Borrelia, Bacillus anthracis*, MRSA, etc., Mycoplasma lipid antigen, peptide hormone such as human chorionic gonadotropin (hCG), etc., steroid such as steroid hormone, etc., biologically active amines such as epinephrine, morphine, etc., vitamins such as B-vitamins, etc., prostaglandins, antibiotics such as tetracycline, etc., toxin produced by bacteria and the like, various tumor markers, agricultural chemical, anti-*Escherichia coli* antibody, anti-*Salmonella* antibody, anti-*Staphylococcus* antibody, anti-*Campylobacter* antibody, anti-*Clostridium perfringens* antibody, anti-*Vibrio parahemolytica* antibody, anti-verotoxin antibody, anti-human transferrin antibody, anti-human albumin antibody, anti-human immunoglobulin antibody, anti-microglobulin antibody, anti-CRP antibody, anti-troponin antibody, anti-HCG antibody, anti-*Chlamydia trachomatis* antibody, anti-streptolysin O antibody, anti-*Helicobacter pylori* antibody, anti-β-glucan antibody, anti-HBe antibody, anti-HBs antibody, anti-adenovirus antibody, anti-HIV antibody, anti-rotavirus antibody, anti-influenza virus antibody, anti-parvovirus antibody, anti-RS virus antibody, anti-RF antibody, complementary nucleotide to nucleic acid component derived from pathogenesis microorganism and the like.

The specimen sample to be analyzed by the method of the present invention includes, but not limited to, biological sample such as a solution, which comprises a fluid collected by wiping pharynx or nasal cavity, suspended in an appropriate buffer, cavity aspirate, feces suspension, blood plasma, blood serum, urine, saliva, amniotic fluid, spinal fluid, pus, organ extract, various tissue extracts and the like, food extract, culture supernatant, clean water, sewage, lake water, fluvial water, sea water, soil extract, sludge extract and a solution thereof diluted by an appropriate buffer. In addition, said buffer can contain from 0.01 to 20 wt % of surfactant. The surfactant that can be used herein includes, but not limited to, TritonX-100: polyethylene glycol mono-p-isooctylphenylether (Nacalai Tesuque Inc.), Tween 20: polyoxyethylene sorbitan monolaurate (Nacalai Tesuque Inc.), Tween 80: polyoxyethylene sorbitan monooleate (Nacalai Tesuque Inc.), NP-40: Nonidet P-40 (Nacalai Tesuque Inc.), Zwittergent: Zwittergent 3-14 (Calbiochem Co. Ltd.), SDS: sodium dodecyl sulfate (Nacalai Tesuque Inc.), CHAPS:3-[(3-cholamidopropyl)dimethylammonio]propanesulfonate (DOJINDO Inc.) and the like, or mixture of two or more thereof.

[Capture-Substance]

A capture-substance to capture an analyte is a substance which binds with the analyte through a specific reaction such as antigen-antibody reaction to form a complex. It is natural, therefore, that the capture-substance to be used varies depending on the kind of analyte. But, in general, when the analyte is bacterium, virus, hormone, other clinical marker and the like, polyclonal antibody, monoclonal antibody and the like which react with the analyte specifically may be used as capture-substance. Examples of capture-substance further include virus antigen, virus-like particle, a protein expressed by a gene recombinant *E. coli*., a protein expressed by a gene recombinant yeast and the like. The method to allow such a capture-substance to bind with the surface of the above-mentioned membrane may be a physical adsorption or the way via a chemical bond. A membrane bound with a capture-substance is prepared, for example, by adsorbing a solution of the capture-substance diluted in a buffer or the like onto the membrane followed by drying the membrane.

[Simple Membrane Assay Kit]

The simple membrane assay kit according to the present invention is a kit which is used in the above-mentioned simple membrane assay method according to the present invention. The simple membrane assay kit according to the present invention comprises at least (1) and (2):

(1) a filter; and (2) an assay device equipped with a membrane bound with a capture-substance to capture an analyte.

The above-mentioned filter is more preferably attached to the above-mentioned filter tube for specimen sample.

The kit may further comprise, if necessary, a specimen suspension, a washing composition, and/or a labeled detection-reagent. In addition, when the label of the labeled detection-reagent is an enzyme label, the kit can comprise a substrate for the enzyme, reaction-terminating solution and the like as described later.

Moreover, as necessary, a negative control solution which consists of only a buffer to examine the activity of the kit and a positive control which consists of a buffer containing an analyte such as antigenic substance. Furthermore, the kit may comprise a specimen-collecting appliance such as a sterile cotton swab.

[Specimen Suspension]

A specimen is collected from pharynx, nasal cavity or the like of a patient, for example, using a specimen-collecting appliance such as a sterile cotton swab, or nasal cavity aspirate may be used as a specimen. Thus obtained specimen is generally suspended in a specimen suspension to perform the assay. Buffers and the like that are generally used in sample detection or quantitation by an immunological technique such as immunodiffusion method, enzyme immunoassay and agglutination method can be used as the specimen suspension.

More specifically, examples of the specimen suspension include, but not limited to, physiological saline, phosphate-buffered saline (PBS), gelatin added PBS, bovine serum albumin (BSA) added PBS, Good's buffer, calf infusion broth (VIB), heart infusion broth, Eagle's minimum essential medium (EMEM), BSA added EMEM and the like. In addition, a combination of two or more of the above buffers may be used.

Moreover, in addition to the above composition, basic amino acids, inorganic salts and/or surfactants can be added. The use of a specimen suspension containing at least two of basic amino acids, inorganic salts and surfactants is preferable, because the binding to the membrane itself and the nonspecific binding to the capture-substance on the membrane of the components in the specimen sample other than the analyte can be decreased.

[Detection-Reagent]

A detection-reagent, as used herein, is anything that can specifically bind to an analyte to form a complex with the analyte. In addition, a labeled detection-reagent refers to a detection-reagent which has been labeled detectably by some means after formation of a complex with the analyte. For example, when the analyte is an antigenic substance such as virus, an antibody against the virus, which has been labeled with an enzyme or the like may be included. If the detection-reagent has been labeled with an enzyme in this manner, the detection of the complex can be performed by adding a substrate of such enzyme which produces a substance that can be detected by colorimetric method or fluorescence method through a reaction catalyzed by such enzyme. The detection-reagent before it is labeled includes the same substances as those described above for the capture-substance. In addition, the label includes enzyme, fluorescent label, magnetic label, radioactive isotope, gold colloid, colored latex and the like.

When an enzyme label is used, the enzyme label used includes, for example, alkaline phosphatase, peroxidase, glucose-6-phosphate dehydrogenase and the like.

[Substrate]

When an enzyme label is used as the label of a labeled detection-reagent, generally a substrate of such enzyme which produces a substance that can be detected by calorimetric method or fluorescence method through a reaction catalyzed by such enzyme is added. The operative examples include 5-bromo-4-chloro-3-indolylphosphoric acid (BCIP)/nitrotetrazolium blue (NBT), tetramethyl benzidine (TMB) and glucose-6-phosphate NAD+.

[Reaction-Terminating Solution]

The kit according to the present invention may further comprise, if necessary, a reaction-terminating solution in order to terminate a reaction such as a reaction between an enzyme and a substrate. Such a reaction-terminating solution includes, for example, citric acid, sulfuric acid and the like.

EXAMPLE

Example 1

Detection of Influenza Virus by Flow-Through Type Immunochromatographic Assay Method 1. Preparation of Monoclonal Antibody (1) Preparation of Anti-Influenza A type Virus NP Monoclonal Antibody (Mouse)

A spleen was ablated from a BALB/c mouse which had been immunized with purified influenza A type virus antigen and kept for a certain period, and it was fused with mouse myeloma cell (P3×63) by the method of Kohler et al. (Kohler et al., Nature, Vol, 256, pp 495-497 (1975)).

The obtained fused cell (hybridoma) was kept in an incubator at 37° C. and purification (monocloning) of the cell was performed while confirming the antibody activity of the supernatant by ELISA using influenza A type virus NP antigen solid phase plate.

Two of the obtained cells were each administered intraperitoneally to a pristane-treated BALB/c mouse, after about 2 weeks, each ascites containing an antibody was collected. IgG was purified from each of the obtained ascites by ammonium sulfate fractionation to yield two kinds of purified anti-influenza A type virus NP monoclonal antibody.

(2) Preparation of Anti-Influenza B Type Virus NP Monoclonal Antibody (Mouse)

A spleen was ablated from a BALB/c mouse which had been immunized with purified influenza B type virus antigen and kept for a certain period, and it was fused with mouse myeloma cell (P3×63) by the method of Kohler et al. (Kohler et al., Nature, Vol, 256, pp 495-497 (1975)).

The obtained fused cell (hybridoma) was kept in an incubator at 37° C. and purification (monocloning) of the cell was performed while confirming the antibody activity of the supernatant by ELISA using influenza B type virus NP antigen solid phase plate.

Two of the obtained cells were each administered intraperitoneally to a pristane-treated BALB/c mouse, after about 2 weeks, each ascites containing an antibody was collected. IgG was purified from each of the obtained ascites by ammonium sulfate fractionation to yield two kinds of purified anti-influenza B type virus NP monoclonal antibodies.

2. Preparation of Labeled Anti-Influenza Antibody Solution (1) Preparation of Labeled Anti-Influenza A Type Antibody Solution 20 mg of one kind of the purified anti-influenza A type virus NP monoclonal antibody was dialyzed with 0.1 M acetate buffer (pH 3.8) followed by addition of 10 mg of pepsin and Fab' digestive treatment was performed for one hour at 37° C. The treated solution was fractionated through ultrogel AcA44 column to yield purified fraction of anti-influenza A type $F(ab')_2$. The thus obtained fraction was concentrated up to about 10 mg/mL, and then it was mixed with 0.1 M mercaptoethylamine in volume ratio of 10:1 and reduction treatment was performed for 90 minutes at 37° C. The treated solution was fractionated through ultrogel AcA44 column to yield purified fraction of anti-influenza A type Fab' followed by concentration of the fractions up to about 1 mL.

1.5 mL of alkaline phosphatase (10 mg/mL) was dialyzed with 50 mM borate buffer (50 mM boric acid (pH 7.6), 1 mM magnesium chloride, 0.1 mM zinc chloride), and then 0.7 mg of N-(6-maleimidecaproyloxy)succinimide (EMCS; DOJINDO Inc.) was added and then the mixture was allowed to stand for one hour at 30° C. The treated solution was fractionated through Sephadex G-25 column and the first peak was recovered to yield maleimide-alkaline phosphatase followed by concentrating the fractions up to about 1 mL.

The concentrated anti-influenza A type Fab' was mixed with maleimide-alkaline phosphatase in the protein ratio of 1:2.3, the resulting mixture was gently stirred for 20 hours at 4° C. and reacted to yield alkaline phosphatase labeled anti-influenza A type Fab'. The reaction solution was fractionated through AcA44 column and unreacted materials were removed to give purified alkaline phosphatase labeled Fab'.

The purified alkaline phosphatase labeled Fab' was diluted with a solution for diluting labeled antibody comprising 4.5 (W/V) % bovine serum albumin, 5.25 (W/V) % polyethylene glycol 6000, 10 mM Tris hydrochloric acid buffer (pH 7.4), 150 mM sodium chloride, 1.5 (W/V) % Triton X-100, 1.5 mM magnesium chloride and 0.15 mM zinc chloride to 1.0 μg/mL followed by filtration of the solution through filter with 0.22 μm of pore size to yield labeled anti-influenza A type antibody solution.

(2) Preparation of Labeled Anti-Influenza B Type Antibody Solution 20 mg of one kind of the purified anti-influenza B type virus NP monoclonal antibody was dialyzed with 0.1 M acetate buffer (pH 3.8) followed by addition of 10 mg of pepsin and Fab' digestive treatment was performed for one hour at 37° C. The treated solution was fractionated through ultrogel AcA44 column to yield purified fraction of anti-influenza B type $F(ab')_2$. The thus obtained fraction was concentrated up to about 10 mg/mL, and then it was mixed with 0.1 M mercaptoethyl amine in volume ratio of 10:1 and reduction treatment was performed for 90 minutes at 37° C. The treated solution was fractionated through ultrogel AcA44 column to yield purified fraction of anti-influenza B type Fab' followed by concentrating the fraction to about 1 mL.

The concentrated anti-influenza B type Fab' was mixed with maleimide-alkaline phosphatase prepared in paragraph "2.(1)" above in the protein ratio of 1:2.3, the resulting mixture was gently stirred for 20 hours at 4° C. and reacted to yield alkaline phosphatase labeled anti-influenza B type Fab'. The reaction solution was fractionated through AcA44 column and unreacted materials were removed to give purified alkaline phosphatase labeled Fab'.

The purified alkaline phosphatase labeled Fab' was diluted with a solution for diluting labeled antibody comprising 4.5 (W/V) % bovine serum albumin, 5.25 (W/V) % polyethylene glycol 6000, 10 mM Tris hydrochloric acid buffer (pH 7.4), 150 mM sodium chloride, 1.5 (W/V) % Triton X-100, 1.5 mM magnesium chloride and 0.15 mM zinc chloride to 1.0 μg/mL followed by filtrating the solution through filter with 0.22 μm of pore size to yield labeled anti-influenza B type antibody solution.

3. Preparation of Flow-Through Type Membrane Assay Device for Influenza Virus Detection The flow-through type membrane assay device for influenza virus detection whose constitution is the same as shown in FIGS. 1 and 2 was used. A nitrocellulose membrane having 3 μm of pore size (Immunopore manufactured by Whatman corporation, size of 2×3 cm, thickness of 125 μm) was used as the membrane.

Immobilization of an antibody to the membrane was performed by spotting two kinds of antibody solutions onto the nitrocellulose membrane. 12 μL of solution containing 0.2 mg/mL of purified anti-influenza A type virus NP monoclonal antibody that was not used in the "preparation of labeled anti-influenza A type antibody" was filtered through a filter with 0.22 μm of pore size to spot onto A hole of the device. 12 μL of solution containing 1 mg/mL of purified anti-influenza B type virus NP monoclonal antibody that was not used in the "preparation of labeled anti-influenza B type antibody" was filtered through a filter with 0.22 μm of pore size to spot onto B hole of the device. 10 mM Citrate buffer (pH 4.0) was used to dilute the antibodies. Then, the spotted antibodies were dried in a drying chamber at 45° C. for 40 minutes to prepare a membrane assay device for influenza virus detection.

4. Detection of Influenza Virus (1) Detection by Flow-Through Type Membrane Assay Method Fluids were collected by wiping with a sterile cotton swab each nasal cavity of 115 patients who were clinically suspected of an infection with influenza virus, and then were suspended into 1.5 mL of solution having a composition of 50 mM phosphate buffer (pH 7.0), 1.5 M sodium chloride, 1 (W/V) % Triton X-100 and 0.5 (W/V) % bovine serum albumin to prepare a sample for test. The sample was well suspended and then divided into three 40 μL aliquots in three filter tubes for specimen sample. Then the following nozzle was mounted to the tip of each tube, respectively; nozzle 1 comprising a filter of a nitrocellulose membrane with 0.45 μm of pore size sandwiched between two glass fibers with 0.67 μm of pore size (particle retention size); nozzle 2 comprising a filter being a stack of three glass fibers with 0.67 μm of pore size (particle retention size); and nozzle 3 comprising no filter.

Each of the specimen samples was filtered through each nozzle. Then 150 μL of the filtrate was added to each of A hole and B hole of the flow-through type membrane assay device prepared in paragraph "3." above and left to stand until the sample was absorbed completely into a liquid absorption member equipped on the bottom of nitrocellulose membrane. Next, 180 μL aliquot of labeled anti-influenza A type antibody solution was added dropwise into A hole, 180 μL aliquot of labeled anti-influenza B type antibody solution was added into B hole and then kept to stand until each of said antibody solutions was absorbed completely into the liquid absorption member. Then the adapter was removed, a washing solution having a composition of 20 mM phosphate buffer (pH 7.0), 0.5 M sodium chloride, 5 (W/V) % arginine hydrochloride and 1 (W/V) % Triton X-100 was added dropwise into each of A hole and B hole by 150 μL, and then kept to stand until each of said washing solutions was absorbed completely into the liquid absorption member. Subsequently, BCIP/NBT substrate solution (manufactured by Sigma corporation) was added dropwise to each of A hole and B hole by 250 μL to initiate a coloring reaction. After 10 minutes, 100 mM citrate buffer (pH 3.0) was added dropwise to each of A hole and B hole by 150 μL to terminate the reaction. Immediately after termination of the reaction, A hole and B hole were observed from vertical upper direction. If coloring was recognized in only A hole, then influenza A type virus was judged positive, if coloring was recognized in only B hole, then influenza B type virus was judged positive, if coloring was recognized in both of A and B holes, then both influenza A type and B type viruses were judged positive, and if coloring was recognized in neither of the holes, then both of influenza A type and B type viruses were judged negative.

(2) Detection by RT-PCR Method

The remains of the samples for test prepared in paragraph "4.(1)" above were used to determine the presence of influenza virus genes in the specimen by RT-PCR method. RT-PCR method was carried out by Shimizu's method ("Kansen-sho-gaku Zasshi" (The Journal of the Japanese Association for Infectious Diseases), Vol. 71, No. 6, pp 522-526).

(3) Comparison Between Flow-Through Type Membrane Assay Method and RT-PCR Method The comparison of results between the simple membrane assay method according to the present invention and the above-mentioned RT-PCR method are shown in Tables 1 to 3. RT-PCR method has been known to be a method of measurement whose sensitivity and specificity are extremely high, so if the judgment was different from one by RT-PCR method, then it was considered as false positive or false negative.

TABLE 1

Comparison in the case of using nozzle 1

| | | RT-PCR method | | | | |
|---|---|---|---|---|---|---|
| | | A type positive | B type positive | A & B type positive | negative | total |
| membrane assay method | A type positive | 32 | 0 | 0 | 0 | 32 |
| | B type positive | 0 | 18 | 0 | 0 | 18 |
| | A & B type positive | 0 | 0 | 0 | 0 | 0 |
| | negative | 0 | 0 | 0 | 65 | 65 |
| | total | 32 | 18 | 0 | 65 | 115 |

* The numerical value in Table refers to the number of specimens.

TABLE 2

Comparison in the case of using nozzle 2

| | | RT-PCR method | | | | |
|---|---|---|---|---|---|---|
| | | A type positive | B type positive | A & B type positive | negative | total |
| membrane assay method | A type positive | 30 | 0 | 0 | 0 | 30 |
| | B type positive | 0 | 15 | 0 | [3] | 18 |
| | A & B type positive | [2] | [3] | 0 | 0 | 5 |
| | negative | 0 | 0 | 0 | 62 | 62 |
| | total | 32 | 18 | 0 | 65 | 115 |

* The numerical value in Table refers to the number of specimens. In addition, the numerical value in the parenthesis refers to false positive.

TABLE 3

Comparison in the case of using nozzle 3

| | | RT-PCR method | | | | |
|---|---|---|---|---|---|---|
| | | A type positive | B type positive | A & B type positive | negative | total |
| membrane assay method | A type positive | 5 | 0 | 0 | 0 | 5 |
| | B type positive | 0 | 2 | 0 | [18] | 20 |
| | A & B type positive | [27] | [16] | 0 | [35] | 78 |
| | negative | 0 | 0 | 0 | 12 | 12 |
| | total | 32 | 18 | 0 | 65 | 115 |

* The numerical value in Table refers to the number of specimens. In addition, the numerical value in the parenthesis refers to false positive.

In the case of using nozzle 1, the results by the membrane assay method were completely identical with the results by RT-PCR method and there was no false positive result. In the case of using nozzle 2, the incidence of false positivity was 7% (8 specimens in 115 specimens (total number of false positive specimens in the parenthesis in Table 2)) but the remaining results were agreed with the results by RT-PCR method. On the other hand, in the case of using nozzle 3, the incidence of false positivity was 83% (96 specimens in 115 specimens (total number of false positive specimens in the parenthesis in Table 3)).

Example 2

Detection of Influenza Virus by Lateral-Flow Type Immunochromatographic Assay Method 1. Preparation of Monoclonal Antibody (1) Preparation of Anti-Influenza A Virus NP Monoclonal Antibody (Mouse)

This antibody was prepared in the same manner as the method described in [Example 1] 1.(1).

(2) Preparation of Anti-Influenza B Type Virus NP Monoclonal Antibody (Mouse)

This antibody was prepared in the same manner as the method described in [Example 1] 1.(2).

2. Preparation of Labeled Anti-Influenza Antibody (1) Preparation of Labeled Anti-Influenza A Type Antibody 20 mg of one kind of the purified anti-influenza A type virus NP monoclonal antibodies was dialyzed with 0.1 M acetate buffer (pH 3.8) followed by addition of 10 mg of pepsin and Fab' digestive treatment was performed for one hour at 37° C. The treated solution was fractionated through ultrogel AcA44 column to yield purified fraction of anti-influenza A type $F(ab')_2$. The thus obtained fraction was concentrated up to about 10 mg/mL, and then it was mixed with 0.1 M mercaptoethylamine in volume ratio of 10:1 and reduction treatment was performed for 90 minutes at 37° C. The treated solution was fractionated through ultrogel AcA44 column to yield purified fraction of anti-influenza A type Fab' followed by concentration of the fraction up to about 1 mL.

1.5 mL of alkaline phosphatase (10 mg/mL) was dialyzed with 50 mM borate buffer (50 mM boric acid (pH 7.6), 1 mM magnesium chloride, 0.1 mM zinc chloride), and then 0.7 mg of N-(6-maleimidecaproyloxy)succinimide (EMCS; DOJINDO Inc.) was added and the mixture was allowed to stand for one hour at 30° C. The treated solution was fractionated through Sephadex G-25 column and the first peak was recovered to yield maleimide-alkaline phosphatase followed by concentration of the fraction up to about 1 mL.

The concentrated anti-influenza A type Fab' was mixed with maleimide-alkaline phosphatase in the protein ratio of 1:2.3, the resulting mixture was gently stirred for 20 hours at 4° C. and reacted to yield alkaline phosphatase labeled anti-influenza A type Fab'. The reaction solution was fractionated through AcA44 column and unreacted materials were removed to give purified alkaline phosphatase labeled Fab'.

(2) Preparation of Labeled Anti-Influenza B Type Antibody 20 mg of one kind of the purified anti-influenza B type virus antibodies was dialyzed with 0.1 M acetate buffer (pH 3.8) followed by addition of 10 mg of pepsin and Fab' digestive treatment was performed for one hour at 37° C. The treated solution was fractionated through ultrogel AcA44 column to yield purified fraction of anti-influenza B type $F(ab')_2$. The thus obtained fraction was concentrated up to about 10 mg/mL, and then it was mixed with 0.1 M mercaptoethylamine in volume ratio of 10:1 and reduction treatment was performed for 90 minutes at 37° C. The treated solution was fractionated through ultrogel AcA44 column to yield purified fraction of anti-influenza B type Fab' followed by concentrating the fraction to about 1 mL.

The concentrated anti-influenza B type Fab' was mixed with maleimide-alkaline phosphatase prepared in 2-(1) in the protein ratio of 1:2.3, the resulting mixture was gently stirred for 20 hours at 4° C. and reacted to yield alkaline phosphatase labeled anti-influenza B type Fab'. The reaction solution was fractionated through AcA44 column and unreacted materials were removed to give purified alkaline phosphatase labeled Fab'.

3. Preparation of Lateral-Flow Type Membrane Assay Device for Influenza Virus Detection The lateral-flow type membrane assay device for influenza virus detection whose constitution is the same as shown in FIGS. 5 and 6 was used. Membrane "j" consists of a nitrocellulose membrane having 5 μm of pore size (PuraBind manufactured by Whatman corporation, size of 5×50 mm, thickness of 200 μm). 2.0 μL of solution containing 1 mg/ml of purified anti-influenza B type virus NP monoclonal antibody that was not used in the "preparation of labeled anti-influenza B type antibody" was coated on a line pattern (width of 1.0 mm) onto "k" position 15 mm apart from one end of the membrane "j" (hereinafter this end is referred to as "downstream end"), and 2.0 μL of solution containing 0.2 mg/ml of purified anti-influenza A type virus NP monoclonal antibody that was not used in the "preparation of labeled anti-influenza A type antibody" was coated on a line pattern (width of 1.0 mm) onto "l" position 18 mm apart from said downstream end. In these coating steps, 10 mM citrate buffer (pH 4.0) was used to dilute the solid phase antibodies and the solution was filtered through a filter with 0.22 μm of pore size immediately before immobilization. After the solution was coated on the membrane, it was dried in a drying chamber at 45° C. for 40 minutes.

Then, members were fixed and plastic backing sheet "m" (manufactured by BioDot corporation) was fitted onto the opposite side to the surface coated with antibody of the membrane in order to increase the strength.

Next, each of the labeled anti-influenza A type antibody and labeled anti-influenza B type antibody prepared in the paragraph "2." above (each concentration was 2 μg/mL) was dropped by 12 μL onto cellulose/glass fiber pad (WF 1.5 manufactured by Whatman corporation, 7 mm×10 mm, thickness of 1.4 mm) and dried for 40 minutes in a drying chamber at 45° C. This pad was fixed on a position 23 mm apart from the downstream end to make sample-receiving pad "g". Cellulose/glass fiber pad (WF 1.5 manufactured by Whatman corporation, 7 mm×15 mm, thickness of 1.4 mm) was fixed on a position where 2 mm of the upstream end of the membrane was overlapped to make substrate-receiving pad "h".

Then, Cellulose/glass fiber pad (WF 1.5 manufactured by Whatman corporation, 10 mm×20 mm, thickness of 1.5 mm) was fixed on a position where 5 mm of the downstream end of the membrane was overlapped to make absorption pad "i".

4. Detection of Influenza Virus (1) Detection by Lateral-Flow Type Membrane Assay Method Fluids were collected by wiping with a sterile cotton swab each nasal cavity of 92 patients who were clinically suspected of an infection with influenza virus, and then were suspended into 0.8 mL of solution having a composition of 20 mM Tris-HCl buffer (pH 8.0), 0.6 M sodium chloride, 1 (W/V) % Triton X-100, 2.0 (W/V) % L-arginine hydrochloride and 1.0 (W/V) % bovine serum albumin to prepare a sample for test. The sample was well suspended and then divided into three 200 μL aliquots in each of three filter tubes for specimen sample. Then the following nozzle was mounted to the tip of each tube, respectively; nozzle 1 comprising a filter of a nitrocellulose membrane with 0.45 μm of pore size sandwiched between two glass fibers with 0.67 μm of pore size (particle retention size); nozzle 4 comprising a filter being a stack of three glass fibers with 1.0 μm of pore size (particle retention size); and nozzle 3 comprising no filter.

Each of the specimen samples was filtered through each nozzle followed by addition of 60 μL aliquot to the sample-receiving pad of the lateral-flow type membrane assay device prepared in paragraph "3." above and was left to stand for 3 minutes. Then, 60 μL of BCIP/NBT substrate solution (manufactured by Sigma corporation) was added dropwise to initiate coloring reaction. After 10 minutes, the position of "e" and "f" in FIGS. 5 and 6 were observed from vertical upper direction. If coloring was recognized in only "e" position, then influenza B type virus was judged positive, if coloring was recognized in only "f" position, then influenza A type virus was judged positive, if coloring was recognized in both of "e" and "f" positions, then both influenza A type and B type viruses were judged positive, and if coloring was recognized in neither of the positions, then both of influenza A type and B type viruses were judged negative.

(2) Detection by RT-PCR Method

The remains of samples for test prepared in paragraph "4.(1)" was used to determine the presence of influenza virus genes in the specimens by RT-PCR method. RT-PCR method was carried out by Shimizu's method (The Journal of the Japanese Association for Infectious Diseases, Vol. 71, No. 6, pp 522-526).

(3) Comparison Between Lateral-Flow Type Membrane Assay Method and RT-PCR Method The comparison of results between the simple membrane assay method according to the present invention and the above-mentioned RT-PCR method are shown in Tables 4 to 6. RT-PCR method has been known to be a method of measurement whose sensitivity and specificity are extremely high, so if the judgment was different from one by RT-PCR method, then it was considered as false positive or false negative.

TABLE 4

Comparison in the case of using nozzle 1

| | | RT-PCR method | | | | |
|---|---|---|---|---|---|---|
| | | A type positive | B type positive | A & B type positive | negative | total |
| membrane assay method | A type positive | 26 | 0 | 0 | 0 | 26 |
| | B type positive | 0 | 11 | 0 | 0 | 11 |
| | A & B type positive | 0 | 0 | 0 | 0 | 0 |
| | negative | 0 | 0 | 0 | 55 | 55 |
| | total | 26 | 11 | 0 | 55 | 92 |

* The numerical value in Table refers to the number of specimens.

TABLE 5

Comparison in the case of using nozzle 4

| | | RT-PCR method | | | | |
|---|---|---|---|---|---|---|
| | | A type positive | B type positive | A & B type positive | negative | total |
| membrane assay method | A type positive | 25 | 0 | 0 | 0 | 30 |
| | B type positive | 0 | 9 | 0 | [2] | 11 |
| | A & B type positive | [1] | [2] | 0 | 0 | 3 |
| | negative | 0 | 0 | 0 | 53 | 53 |
| | total | 26 | 11 | 0 | 55 | 92 |

* The numerical value in Table refers to the number of specimens. In addition, the numerical value in the parenthesis refers to false positive.

TABLE 6

Comparison in the case of using nozzle 3

| | | RT-PCR method | | | | |
|---|---|---|---|---|---|---|
| | | A type positive | B type positive | A & B type positive | negative | total |
| membrane assay method | A type positive | 18 | 0 | 0 | 0 | 18 |
| | B type positive | 0 | 7 | 0 | [10] | 17 |
| | A & B type positive | [8] | [4] | 0 | [7] | 19 |
| | negative | 0 | 0 | 0 | 38 | 38 |
| | total | 26 | 11 | 0 | 55 | 92 |

* The numerical value in Table refers to the number of specimens. In addition, the numerical value in the parenthesis refers to false positive.

In the case of using nozzle 1, the results by the membrane assay method were completely identical with the results by RT-PCR method and there was no false positive result. In the case of using nozzle 4, the incidence of false positivity was 5% (5 specimens in 92 specimens (total number of false positive specimens in the parenthesis in Table 5)) and the remaining results were agreed with the results by RT-PCR method. On the other hand, in the case of using nozzle 3, the incidence of false positivity was 32% (29 specimens in 92 specimens (total number of false positive specimens in the parenthesis in Table 6)).

THE EFFECT OF THE PRESENT INVENTION

In accordance with the present invention, a highly reliable simple membrane assay method which can prevent an occurrence of false positivity has been established.

INDUSTRIAL APPLICABILITY

The simple membrane assay method or simple membrane assay kit according to the present invention can be used for a simple test in which an analyte such as pathogen and antibody in a specimen collected in a medical scene or by an individual can be detected or quantitated in situ rapidly and precisely.

The invention claimed is:

1. A membrane assay method for detecting or quantitating an analyte in a specimen sample using (i) an assay device equipped with a membrane bound with a capture-substance to capture the analyte and (ii) a filter tube consisting of a body part and a tip part, wherein the body part of the filter tube is made of flexible material, wherein the method comprises the steps of:

(i) placing a suspension of specimen in the body part of the filter tube;

(ii) attaching the tip part equipped with a filter to the body part;

(iii) filtering the specimen sample through the filter by applying pressure in the filter tube by hand;

(iv) then dropping the filtrate onto the membrane; and (v) detecting or quantitating the presence of the analyte in the specimen sample, wherein a pore size or particle retention size of the membrane is not less than a pore size or particle retention size of the filter.

2. The method according to claim 1, wherein the specimen sample has been collected from pharynx or nasal cavity of a patient.

3. The method according to claim 1, wherein the flexible material is selected from the group consisting of polyethylene and polyethylene terephthalate.

4. The method according to claim 1, wherein the material of the filter is selected from the group consisting of nonwoven fabric, paper, glass fiber, silica fiber, nitrocellulose, cellulose ester, a mixture of nitrocellulose and cellulose ester, polyether sulfone, polysulfone, polyethylene tetrafluoride, polyvinylidene fluoride, polycarbonate, polypropylene, polyamide, 6,6-nylon, polyester, cotton, stainless steel fiber and a combination thereof.

5. The method according to claim 1, wherein the pore size or the particle retention size of the filter is from 0.2 to 8.0 μm.

6. The method according to claim 1, wherein the filter is a glass fiber filter, a nitrocellulose filter, or a combination of glass fiber filter and nitrocellulose filter.

7. The method according to claim 1, wherein the material of the membrane is selected from the group consisting of nonwoven fabric, paper, nitrocellulose, glass fiber, silica fiber, cellulose ester, polyether sulfone, polysulfone, polyethylene tetrafluoride, polyvinylidene fluoride, polycarbonate, polypropylene, polyamide, 6,6-nylon and a mixture of cellulose ester and nitrocellulose, and that the pore size or the particle retention size of the membrane is not less than the pore size or the particle retention size of the filter and is from 0.3 to 15 μm.

8. The method according to claim 7, wherein the material of the membrane is nitrocellulose and its pore size is from 0.4 to 12 μm.

9. The method according to claim 1, wherein the analyte is an influenza virus.

10. The method according to claim 1, which is a flow-through type or lateral-flow type membrane assay method.

11. The flow-through type membrane assay method according to claim 10, wherein the pore size or the particle retention size of the filter is from 0.2 to 4.0 μm.

* * * * *